(12) United States Patent
Bartholomew

(10) Patent No.: US 6,594,018 B1
(45) Date of Patent: Jul. 15, 2003

(54) MINIATURE INTEGRATED MULTIPLE CHANNEL SURFACE PLASMON RESONANCE LIQUID SENSOR

(75) Inventor: Dwight U. Bartholomew, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 240 days.

(21) Appl. No.: 09/774,970

(22) Filed: Jan. 31, 2001

Related U.S. Application Data

(60) Provisional application No. 60/179,632, filed on Feb. 1, 2000.

(51) Int. Cl.⁷ ................................................ G01N 21/55
(52) U.S. Cl. ...................................................... 356/445
(58) Field of Search ................................ 356/445–448, 356/128

(56) References Cited

U.S. PATENT DOCUMENTS

| | | | |
|---|---|---|---|
| 5,313,264 A | 5/1994 | Ivarsson et al. | |
| 5,629,774 A | 5/1997 | Peacock et al. | |
| 5,946,083 A | 8/1999 | Melendez et al. | |
| 5,991,048 A | * 11/1999 | Karlson et al. | 356/445 |
| 5,999,262 A | * 12/1999 | Dobschal et al. | 356/456 |
| 6,008,893 A | 12/1999 | Roos et al. | |
| 6,462,809 B1 | * 10/2002 | Ryan et al. | 356/128 |

* cited by examiner

*Primary Examiner*—Michael P. Stafira
(74) *Attorney, Agent, or Firm*—April M. Mosby; Wade James Brady, III; Frederick J. Telecky, Jr.

(57) ABSTRACT

A surface plasmon resonance sensor capable of determining the property of several liquids at varying times or simultaneously without the need for a reflecting surface is incorporated herein. This sensor includes at least one electromagnetic radiation source which generates a beam of electromagnetic radiation that passes through a filter and a polarizer disposed between the source and an array of detectors. The filter prevents electromagnetic radiation at the absorbed frequency from striking the array. A film of a conductive material capable of sustaining surface plasmon resonance has a first surface and a second surface. Liquids are deposited on the first surface, while the second surface reflects at least part of the beam of electromagnetic radiation generated by the source. The array of electromagnetic radiation detectors detect part of the beam of electromagnetic radiation to make a determination of a property of the plurality of liquids and produce an output signal in response to the received portion of the reflected electromagnetic radiation indicative of the presence of, or representative of the concentration or a concentration range of, the liquid. This array may be one, two, or three dimensional. In the instance where more than one electromagnetic radiation sources are used, a controller switches each source on and off so that all sources are turned on simultaneously or in a sequential order.

16 Claims, 2 Drawing Sheets

MINIATURE INTEGRATED MULTIPLE CHANNEL SURFACE PLASMON RESONANCE LIQUID SENSOR

CROSS REFERENCE TO RELATED APPLICATIONS

This application claims the benefit of Provisional application Ser. No. 60/179,632, filed Feb. 1, 2000.

This invention is related to our applications, Ser. Nos. 08/820,730 now abandoned and Ser. No. 09/732,150, filed Mar. 19, 1997 and Dec. 7, 2000, respectively.

FIELD OF THE INVENTION

This invention relates generally to the field of surface plasmon resonance sensors and, more particularly, to the field of sensors used in the fields of chemical, biochemical, biological or biomedical analysis, process control, pollution detection and control, and other similar areas.

BACKGROUND OF THE INVENTION

Surface plasmon resonance is an optical surface phenomenon that has been employed in sensors used in the fields of chemical, biochemical, biological or biomedical analysis. A surface plasmon is a surface charge density wave at the surface of a thin conducting film. This resonance can be observed when a polarized beam of monochromatic electromagnetic radiation is totally internally reflected from a dielectric interface having a thin metal film formed thereon. Usually the interface comprises a smooth surface of a transparent body such as glass. The electromagnetic radiation internally reflected by the interface has a minimum intensity at a particular angle referred to as resonant angle. This angle is determined by the dielectric conditions adjacent the metal film and the properties of the film itself.

The basis for the use of surface plasmon resonance for sensing is the fact that the oscillation of a surface-plasma of free electrons which exists at a conductor-dielectric boundary is affected by the refractive index of the material adjacent the conducting film surface on the side thereof opposite the reflected polarized electromagnetic radiation. For a given wavelength of radiation, the resonance occurs when the angle of incidence of the polarized radiation has a particular value and this value, dependent on the refractive index, gives rise to changes in the angle at which surface plasmon resonance occurs. When polarized electromagnetic radiation strikes the thin metal film at the resonance angle, the intensity of the reflected electromagnetic radiation therefrom is minimized. A reflecting surface reflects the electromagnetic radiation reflected from the surface upon which the surface plasmon resonance occurs towards a one dimensional array of detectors. Hence, by detecting the angle at which the minimum intensity of electromagnetic radiation occurs, the refractive index of the material adjacent the film can be determined. The usefulness of this approach, however, has been limited due to the criticality of the reflecting surface. In addition, the number of materials capable of being detected directly corresponding to the number of channels is limited.

Therefore, it would be desirable to have a surface plasmon resonance sensor having a multiplicity of channels without the need for a reflecting surface.

SUMMARY OF THE INVENTION

The problems associated with earlier sensors are overcome by the present invention which provides a surface plasmon resonance sensor capable of determining the property of several liquids at varying times or simultaneously without the need for a reflecting surface. The sensor includes an electromagnetic radiation source which generates a beam of electromagnetic radiation that passes through a filter and a polarizer disposed between the source and an array of detectors. The filter prevents electromagnetic radiation at the absorbed frequency from striking the array. A film of a conductive material capable of sustaining surface plasmon resonance has a first surface and a second surface. Liquids are deposited on the first surface, while the second surface reflects at least part of the beam of electromagnetic radiation generated by the source. The array of electromagnetic radiation detectors detect part of the beam of electromagnetic radiation to make a determination of a property of the plurality of liquids and produce an output signal in response to the received portion of the reflected electromagnetic radiation indicative of the presence of, or representative of the concentration or a concentration range of, the liquid. This array may be one, two, or three dimensional.

Furthermore, the surface plasmon resonance sensor may include a number electromagnetic radiation sources to increase the number of channel capacity. Another embodiment may provide controller coupled to the number of electromagnetic radiation sources for switching each source on and off so that all sources are turned on simultaneously or in a sequential order.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF PREFERRED EMBODIMENTS

Figure 1:
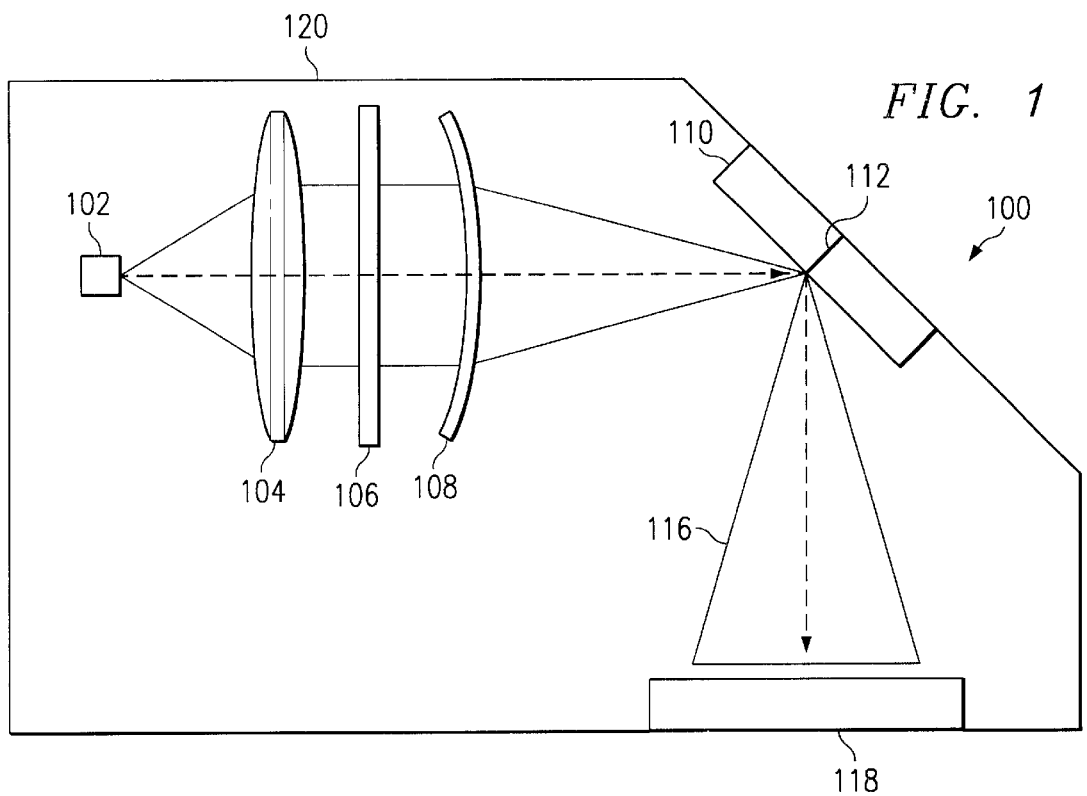
FIG. 1 a 300 channel surface plasmon resonance sensor in accordance with the present invention.

In the embodiment shown in FIG. 1 illustrates one embodiment of a surface plasmon resonance sensor 100 in accordance with the present invention. Sensor 100 has the capability to determine the property of each of a plurality of liquids. Sensor 100 includes an electromagnetic radiation source 102, a spherical lens 104, a polarizing filter 106, a cylindrical lens 108 a surface plasmon resonance structure 110 and a plurality of electromagnetic radiation detectors mounted in a two dimensional array 118. Electromagnetic radiation source 102, which may comprise a light emitting diode (LED), a laser diode or any other suitable source of radiation.

In operation, liquids are first deposited on the exposed surface of structure 110. The emitted beam from the electromagnetic radiation source 102 passes through the spherical lens 104. The polarizing filter 106 is disposed between the cylindrical lens 108 and the spherical lens 104 for polarizing the emitted beam. The polarized radiation passes through the cylindrical lens towards a surface plasmon resonance (SPR) structure 110 having a first and a second surface where the beam is focused on line 112. The surface plasmon resonance structure 110 may comprise a thin layer of conductive or non-conductive material able to sustain surface plasmon having a substantially uniform thickness. Non-conductive material examples may be one-dimensional photonic bandgap material such as, thin bilayers of titanium dioxide and silicon dioxide, and conductive material examples may be copper, silver, or gold. Structure 110 is preferably planar although other configurations, such as convex or concave configurations, or featured with steps, periodic or non-periodic, can also be utilized. One embodiment may comprise a film of gold approximately 275 angstroms thick. The thickness of a surface plasmon resonance layer may vary form about 200 to about 600 angstroms and still permit surface plasmon resonance to occur. The specific film thickness is determined by experimentation with respect to the frequency of the radiation for the source 102 and the properties of the conductive material used for structure 110. As is known is the art, when radiation strikes a thin conductive film at the interface of an insulator, the intensity of reflection therefrom is a function of the angle of incidence of the radiation onto the film and the refractive index of the material or liquid in contact with the other side of the film. Hence, by determining the angle at which minimum reflectance occurs, it is possible to determine the index of refraction of the material on the side of the structure 110 opposite the side in which the beam is reflected.

In accordance with the utilizing the principal of operation described above, the configuration of FIG. 1 produces polarized beam which is reflected from the thin surface plasmon resonance structure 110. The polarized beam passes though a cylindrical lens 108. For optical radiation, the detector array 118 produces a signal on an output pin (not shown) with an electrical signal that is proportional to the intensity of the radiation striking the detector. By measuring the voltage at each detector and the angle that the radiation striking the detector intercepts the surface plasmon resonance structure 110, one can produce a plot of reflected radiation intensity as a function of angle. That plot can be correlated to the index of refraction of the substance on the side of the surface plasmon resonance structure 110 opposite the side where the beam is reflected.

Those of skill in the art will recognize that the physical location of the elements illustrated in FIG. 1 can be moved or relocated while retaining the function described above. For example, the location and shape of the surface plasmon resonance structure 110 can take on other configurations and locations so long as radiation strikes the structure 110 and the intensity of the radiation reflected therefrom is measured as a finction of the angle of the radiation striking the surface plasmon resonance structure 110.

Figure 2:
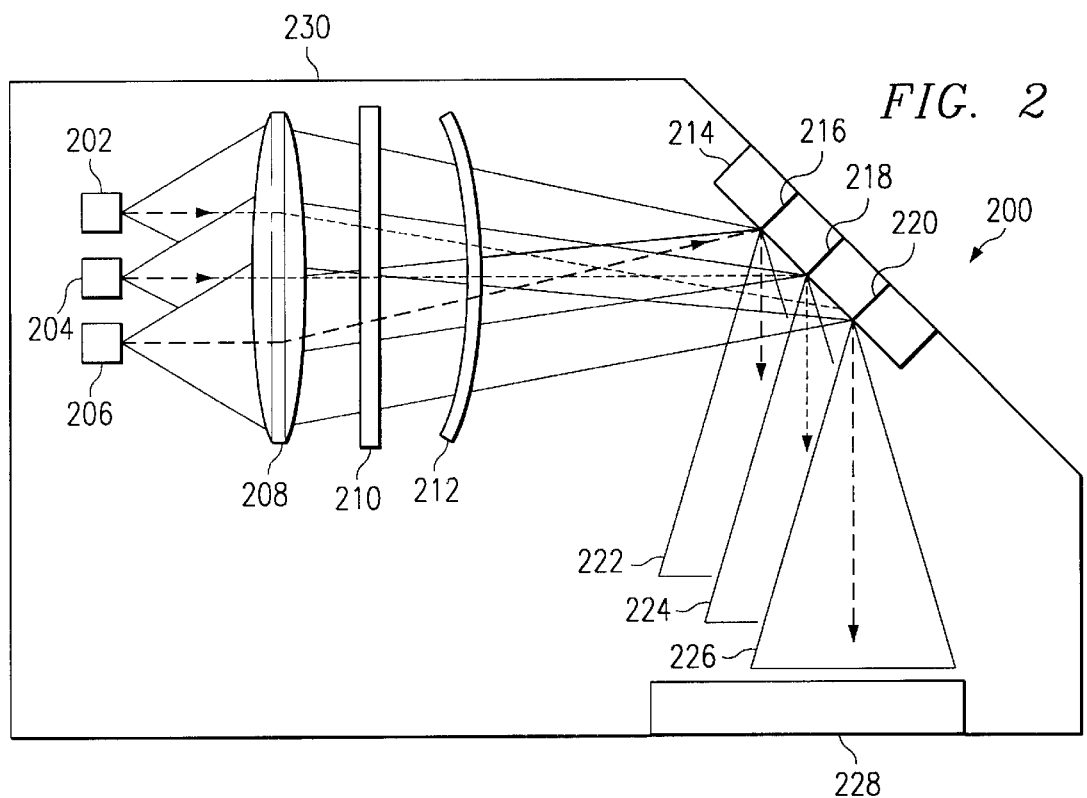
FIG. 2 a 900 channel surface plasmon resonance sensor in accordance with the present invention.

FIG. 2 illustrates an alternative embodiment 200 in accordance with the present invention. The alternative embodiment 200 includes a plurality of electromagnetic radiation sources 202, 204, and 206. Accordingly, those of skill in the art will recognize that the number of electromagnetic radiation sources may vary in number and the electromagnetic radiation emitted may vary in wavelength. In operation, a control means (not shown) may turn on and off electromagnetic radiation sources 202, 204, and 206 such that only one source emits a beam at a time. In the alternative, if each of the sources 202, 204, and 206 emit electromagnetic radiation at varying wavelengths, the sources 202, 204, and 206 may emit beams simultaneously. In the case of single emission, one electromagnetic radiation source 202, 204, or 206 emits a beam that is disposed upon spherical lens 208. The filtered beam propagates to a polarizer 210. The polarized beam propagates to cylindrical lens 212. Each polarized beam reflects off of a surface plasmon resonance structure 214 at a focus line 216, 218, and 220 corresponding to the beams emitted from electromagnetic radiation sources 206, 204 and 202, respectively.

Those skilled in the art will recognize that when a beam of electromagnetic radiation passes from one medium to another in a non-normal direction, the direction of the beam leaving the junction on one side thereof usually leaves at an angle different from the angle the radiation enters the junction. This phenomenon is caused by the fact that the index of refraction of the body/gas on one side of the junction is different from the index of refraction of the gas/body on the other side of the junction.

Thus, as a liquid is applied to the surface opposite the side of the surface plasmon resonance structure 214 in which the beam reflects, the respective beams corresponding to electromagnetic radiation sources 202, 204 and 206 reflect at an angle indicative of the substance that is being measured or at the resonance angle. The reflected beams 222, 224, and 226 are received by a two dimensional electromagnetic radiation detector array 228. The electromagnetic radiation detector array 228 may be one or three dimensional. Each electromagnetic radiation detector in array 228 detects a different portion of the electromagnetic radiation and determines a property of the portion of electromagnetic radiation detected. Based upon these properties, a property of one of the liquids applied to the surface of structure 214 can be determined. In the single emission mode of operation, this sequence may be repeated for each of the electromagnetic radiation sources 202, 204 and 206 and liquids.

Simultaneous transmission of the electromagnetic radiation beams emitted from electromagnetic radiation sources 202, 204, and 206 can occur if the wavelength of the electromagnetic radiation differs between each electromagnetic radiation source 202, 204, and 206. Possibly another embodiment may include a control means (not shown) to turn electromagnetic radiation sources 202, 204 and 206 on and off in the case where each source emits electromagnetic radiation at the same wavelength so as not to generate interference between the propagating beams of electromagnetic radiation.

Figure 3:
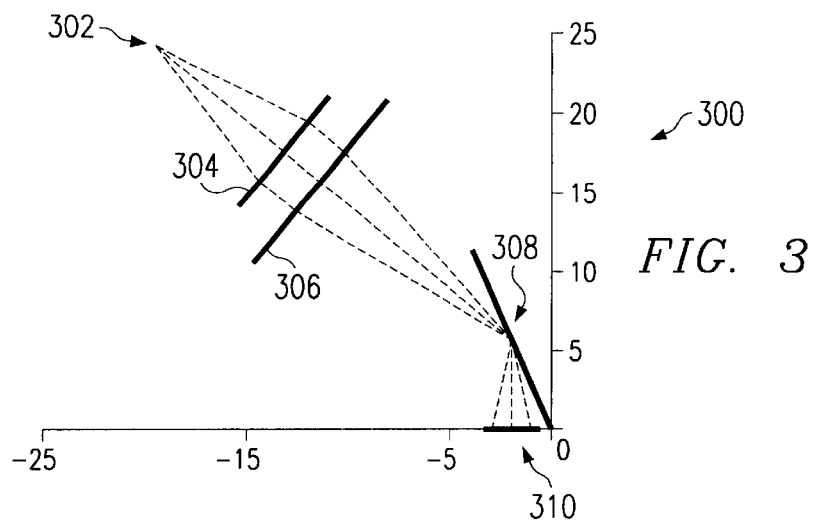
FIG. 3 illustrates a non-planar embodiment in accordance with the present invention.

FIG. 3 illustrates a non-planar embodiment 300 in accordance with the present invention. Electromagnetic radiation source 302 emits a beam which is filtered through spherical lens 304. The beam is filtered through a cylindrical lens 306 and is directed towards a surface plasmon resonance structure 308. The beam reflects off of surface plasmon resonance structure 308 and is received by a two dimensional array of electromagnetic radiation detectors 310. Alternatively, a plurality of electromagnetic radiation sources may be used in lieu of one electromagnetic radiation source 302. In addition, the filter lenses 304 and 306 may vary in orientation, i.e., convex, spherical, cylindrical, etc.

Figure 4:
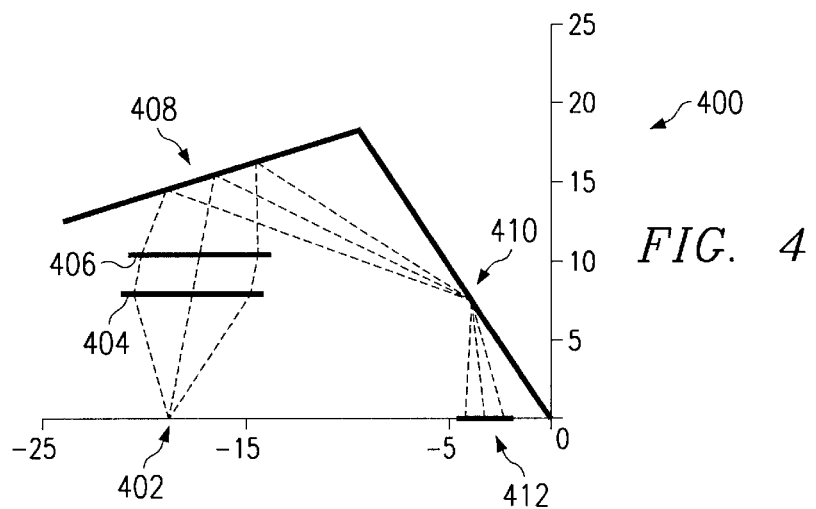
FIG. 4 illustrates a planar embodiment in accordance with the present invention.

FIG. 4 illustrates a planar embodiment 400 in accordance with the present invention. This embodiment 400 includes a electromagnetic radiation source 402 which emits a beam. This beam is filtered by spherical lens 404 and a cylindrical lens 406. Mirror 408 reflects the filtered beam towards a surface plasmon resonance structure 410. Due to the index of refraction the filtered beam is bent and reflected onto a two dimensional array of electromagnetic radiation detectors 412. Alternatively, a plurality of electromagnetic radiation sources may be used in lieu of one electromagnetic radiation source 402. In addition, the filter lenses 404 and 406 may vary in orientation, i.e., convex, spherical, cylindrical, etc.

Figure 5:
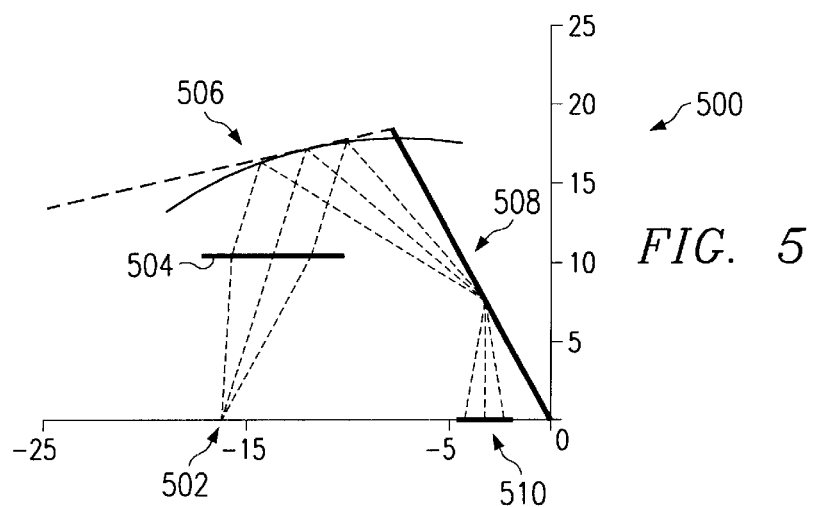
FIG. 5 illustrates a planar embodiment having a curved mirror in accordance with the present invention.

FIG. 5 illustrates a planar embodiment 500 having a curved mirror in accordance with the present invention. Planar embodiment 500 includes electromagnetic radiation source 502 which emits a beam directed towards spherical lens 504. Alternatively, a plurality of electromagnetic radiation sources may be used in lieu of one electromagnetic radiation source 502. The filtered beam propagates towards a cylindrical mirror 506 and is reflected towards a surface plasmon resonance structure 508. The beam reflects off of structure 508 onto two dimensional array of electromagnetic radiation detectors 510. In addition, the filter lens 504 may vary in orientation, i.e., convex, spherical, cylindrical, etc. The mirror 506 may vary in shape as well.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A sensor for determining a property of each of a plurality of liquids, comprising:

an electromagnetic radiation source, said source generating a beam of electromagnetic radiation;

an array of electromagnetic radiation detectors, each detector responsive to detect part of the beam of electromagnetic radiation generated by said source for making a determination of a property of the plurality of liquids;

a polarizer disposed between said source and said array of detectors to polarize the electromagnetic radiation which strikes said array;

a filter disposed between said source and said array to prevent electromagnetic radiation at the frequency absorbed thereby from striking said array; and a film of material capable of sustaining surface plasmon resonance, said film having a first surface and a second surface, said plurality of liquids deposited on said first surface, said second surface reflecting at least part of the beam of electromagnetic radiation generated by said source;

said array of electromagnetic radiation detectors positioned to receive a portion of the electromagnetic radiation reflected from said film and for producing an output signal in response to the received portion of the reflected electromagnetic radiation indicative of the presence of, or representative of the concentration or a concentration range of, the liquid.

2. A sensor of claim 1 further comprising a plurality of electromagnetic radiation sources, wherein each of said plurality of liquids is associated with one of said plurality of sources.

3. A sensor of claim 1 wherein said array is a two dimensional array.

4. A sensor of claim 1 wherein said array is a three dimensional array.

5. A sensor of claim 2 wherein said plurality of electromagnetic radiation sources each generates a beam of electromagnetic radiation of differing wavelength.

6. A sensor of claim 1 wherein said filter is spherical.

7. A sensor of claim 1 wherein said filter is cylindrical.

8. A sensor of claim 1 wherein said material of said film is conductive.

9. A sensor of claim 1 wherein said material of said film is nonconductive.

10. A sensor of claim 1 wherein said film is a conductive material selected form the group consisting of copper, gold, silver and aluminum.

11. A sensor of claim 1 wherein said film is a nonconductive material selected from the group consisting of silicon dioxide and titanium dioxide.

12. A sensor of claim 2 further comprising a control means coupled to each of the plurality of electromagnetic radiation sources for switching on and off each of said plurality of electromagnetic radiation sources such that only one of said plurality of electromagnetic radiation sources emits a beam of electromagnetic radiation at a time.

13. A sensor of claim 12 wherein said control means switches said plurality of electromagnetic radiation sources on and off such that all of said plurality of electromagnetic radiation sources emit electromagnetic radiation at the same time.

14. A sensor of claim 2 further comprising:

an optical housing for encapsulating said plurality of sources of electromagnetic radiation and said array of detectors, said housing comprising a material which is capable of transmitting electromagnetic radiation from said plurality of sources;

said film being disposed on an exterior surface of said optical housing;

said film and said housing being shaped and positioned relative to said plurality of sources and said array of detectors so that radiation from said plurality of sources is reflected by said film and detected by said array of detectors.

15. A sensor of claim 14 further comprising:

at least one optically reflective surface disposed on an exterior surface of said optical housing;

said optical reflective surface, said film and said housing being shaped and positioned relative to said plurality of sources, sensor array and base so that radiation from said plurality of sources is reflected by said film and said optically reflective surface and detected by said sensor array.

16. A sensor of claim 15 wherein said optical reflective surface is cylindrical.

* * * * *